US006436059B1

(12) United States Patent
Zanelli (10) Patent No.: US 6,436,059 B1
(45) Date of Patent: Aug. 20, 2002

(54) DETECTION OF IMD CONTACT AND ALIGNMENT BASED ON CHANGES IN FREQUENCY RESPONSE CHARACTERISTICS

(76) Inventor: Claudio I. Zanelli, 2100 Prospect St., Menlo Park, CA (US) 94025

( * ) Notice: Subject to any disclaimer, the term of this patent is extended or adjusted under 35 U.S.C. 154(b) by 74 days.

(21) Appl. No.: 09/660,057

(22) Filed: Sep. 12, 2000

(51) Int. Cl.[7] .......................... A61B 5/103; A61B 5/117
(52) U.S. Cl. ..................................... 600/587
(58) Field of Search ............................... 600/587, 300, 600/486, 564; 606/170, 159, 1, 169, 171

(56) References Cited

U.S. PATENT DOCUMENTS

| | | | |
|---|---|---|---|
| 4,658,817 A | 4/1987 | Hardy | 128/303.1 |
| 4,936,281 A | 6/1990 | Stasz | 128/660.03 |
| 5,109,830 A | 5/1992 | Cho | 128/4 |
| 5,109,859 A | 5/1992 | Jenkins | 128/662.03 |
| 5,196,006 A | 3/1993 | Klopotek et al. | 606/12 |
| 5,313,950 A | 5/1994 | Ishikawa et al. | 128/662.06 |
| 5,377,682 A | 1/1995 | Ueno et al. | 128/660.1 |
| 5,409,000 A | 4/1995 | Imran | 128/642 |
| 5,544,656 A | 8/1996 | Pitsillides et al. | 128/661.04 |
| 5,662,124 A | 9/1997 | Wilk | 128/898 |
| 5,724,975 A | 3/1998 | Negus et al. | 128/661.09 |
| 5,893,848 A | 4/1999 | Negus et al. | 606/41 |
| 5,911,694 A | 6/1999 | Ikeda et al. | 600/587 |
| 6,019,726 A | 2/2000 | Webb | 600/459 |
| 6,024,703 A | 2/2000 | Zanelli et al. | 600/437 |
| 6,030,377 A | 2/2000 | Linhares et al. | 606/7 |
| 6,102,926 A * | 8/2000 | Tartaglia et al. | 606/170 |
| 6,221,023 B1 * | 4/2001 | Matsuba et al. | 600/486 |

FOREIGN PATENT DOCUMENTS

| | | | |
|---|---|---|---|
| DE | 4433104 | 5/1996 | A61B/5/00 |
| DE | 195 37 084 | 4/1997 | |
| DE | 196 06 610 | 8/1997 | |
| EP | 0764842 | 3/1991 | G01N/3/40 |
| EP | 0 876 796 | 11/1998 | |
| WO | WO 97/25101 | 7/1997 | |
| WO | WO 98/17185 | 4/1998 | |
| WO | WO 98/30144 | 7/1998 | |
| WO | WO 98/38916 | 9/1998 | |

OTHER PUBLICATIONS

G.L. Wojcik, D.K. Vaughan, N.N. Abboud, J. Mould Jr., "Electromechanical Modeling Using Explicit Time–Domain Finite Elements", Preprint of the final article that appeared in IEEE 1993 Ultrasonics Symposium Proceedings, vol. 2, pp. 1107–1112.

S. Omata, "New Type Tactile Sensor for Sending Hardness Like the Human Hand and Its Application for Living Tissue", *Technical Digest of the 9th Sensor Symposium*, pp. 257–260 (1990).

Copy of Search Report in corresponding PCT Application Serial No. PCT/US01/28167, mailed Mar. 13, 2002.

* cited by examiner

*Primary Examiner*—Kevin Shaver
*Assistant Examiner*—Brian Szmal
(74) *Attorney, Agent, or Firm*—James F. Feeney; Shirley L. Church (57) ABSTRACT

A method and apparatus for remotely monitoring the location of an interventional medical device (IMD) which monitors changes in frequency response characteristics of a sensor. Embodiments of the present invention may use changes in the complex impedance properties of the sensor, at antiresonance, or changes in the resonant frequency of an LC circuit to indicate whether or not the IMD is in contact with a tissue surface. The present invention is adapted for use in conjunction with a wide variety of IMDs, and in a wide variety of medical procedures.

30 Claims, 6 Drawing Sheets

DETECTION OF IMD CONTACT AND ALIGNMENT BASED ON CHANGES IN FREQUENCY RESPONSE CHARACTERISTICS

FIELD OF THE INVENTION

The present invention relates to monitoring interventional medical devices (IMDs). More particularly, the present invention relates to monitoring the position of the IMD relative to a tissue surface by observing changes in the frequency response characteristics of a detector.

BACKGROUND OF THE INVENTION

Interventional medical devices (IMDs), such as catheters and surgical lasers are used for many medical procedures. Laparoscopy, the insertion of a fiber optic instrument into the abdomen, is just one relatively common type of IMD procedure. Minimally invasive surgery (MIS) is a term that, as used in this disclosure, encompasses a broader range of such procedures, and in which an IMD is introduced into the patient through a relatively small incision. A major problem inherent with the use of IMDs in MIS procedures is detecting the current location and orientation of the IMD, and remotely guiding it within a patient. It would be desirable to have an apparatus or method that assisted in precisely determining the location and orientation of a wide range of IMDs. It would be particularly desirable to have an apparatus or method for determining when the distal end of the IMD is in contact with and perpendicular to a tissue surface.

U.S. Pat. No. 5,109,859 issued to Jenkins on May 5, 1992 (the '859 patent), discloses an ultrasound guided laser for use in angioplasty. The '859 patent is specifically directed at a method of imaging the lateral walls of arteries for laser ablation procedures and can not easily be adapted to function with a wide range of IMDs.

U.S. Pat. No. 5,313,950 issued to Ishikawa, et al. on May 24, 1994 (the '950 patent), discloses an ultrasonic probe for providing images in hollow objects such as blood vessels. The '950 patent, like the '859 patent, creates images at 90° to the longitudinal axis of the IMD. This lateral imaging provides little data for determining IMD alignment and indicating when the distal end of the IMD is in contact with a tissue surface.

U.S. Pat. No. 5,377,682 issued to Ueno, et al. on Jan. 3, 1995 (the '682 patent) also teaches an ultrasonic probe for imaging perpendicular to the longitudinal axis. Again, there is no description which assists in determining alignment of the probe and indicating when the distal end of the IMD is in contact with a tissue surface.

U.S. Pat. No. 5,893,848 issued to Negus, et al. on Apr. 13, 1999 (the '848 patent), teaches a gauging system for monitoring the depth of an IMD as it penetrates into heart tissue. However, the '848 patent does not provide data on the proximity of the IMD to the tissue surface prior to penetrating the surface, nor does it indicate the angle of the IMD relative to the tissue surface.

U.S. Pat. No. 6,024,703 issued to Zanelli, et al. on Feb. 15, 2000 (the '703 patent), measures the distance between the distal end of the IMD and the tissue surface both prior to contacting the surface and after penetrating the surface. This invention is primarily directed at measuring the distance between a laser IMD that has penetrated the tissue surface and the rear surface of that tissue. It is not as well suited for providing positional data prior to the laser penetrating the tissue, or for indicating when contact has been made between the IMD and the front surface of the tissue. A weakness of the device taught in the '703 patent is the inability to achieve high measurement accuracy when the IMD is very close to, or in contact with, the tissue surface. It would be desirable to accurately determine the IMD proximity to the tissue surface when it is close to the tissue surface, as well as accurately indicating contact with the tissue surface.

SUMMARY OF THE INVENTION

A method and apparatus for remotely monitoring the location of an interventional medical device (IMD) which monitors changes in frequency response characteristics of a sensor. Embodiments of the present invention may use changes in the complex impedance properties of the sensor, at antiresonance, or changes in the resonant frequency of an LC circuit to indicate whether or not the IMD is in contact with a tissue surface. The present invention is adapted for use in conjunction with a wide variety of IMDs, and in a wide variety of medical procedures.

DETAILED DESCRIPTION

The present invention is directed to remotely detecting when an interventional medical device (IMD) is in contact with a tissue surface using changes in the frequency response (FR) characteristics of a sensor mounted on the IMD. Embodiments of the present invention may also remotely detect when an IMD is perpendicular to a tissue surface.

Typically, although not exclusively, the IMD is a tool that is used as part of a minimally invasive surgical (MIS) procedure. MIS procedures, such as laparoscopy, are well known in art. The present invention is not, however, intended to be limited to any particularly surgical procedure. Similarly, the types of IMDs that may be used in conjunction with the present invention is intended to be broad, including, but not limited to, catheters, probes, endoscopes, fiber optic devices, cannules, stylets, needles, laparoscopes and surgical lasers.

As used in the present disclosure, perpendicularity is a measure of whether or not the longitudinal axis of an IMD, at the distal end of the IMD, is at right angles to the plane of the tissue surface at a point where there is contact between the IMD and the tissue surface. As discussed more fully below, the perpendicularity of an IMD is generally defined in three dimensional (3D) space, often using two orthogonal planes passing through the longitudinal axis of the IMD. Degree of perpendicularity is a synonym for perpendicularity and is used in some instances to further emphasize that perpendicularity is a term of measurement.

One application of the present invention is use with a catheter during performance of transmyocardial revascularization (TMR) procedure. This embodiment is chosen because it well illustrates the present invention, and is not intended to indicate a limit of the scope of uses for the present invention. The TMR procedure is well known in the art. TMR involves creating channels in the left ventricle, from inside the heart, to increase the blood and oxygen supply to the heart muscle. Surgical lasers and mechanical devices are some of the many devices used to create the channels. Regardless of the channel creating device used, medical personnel operate the device remotely. That is, the distal end of an IMD which is used to carry out the procedure will be inside the heart.

Figure 1:
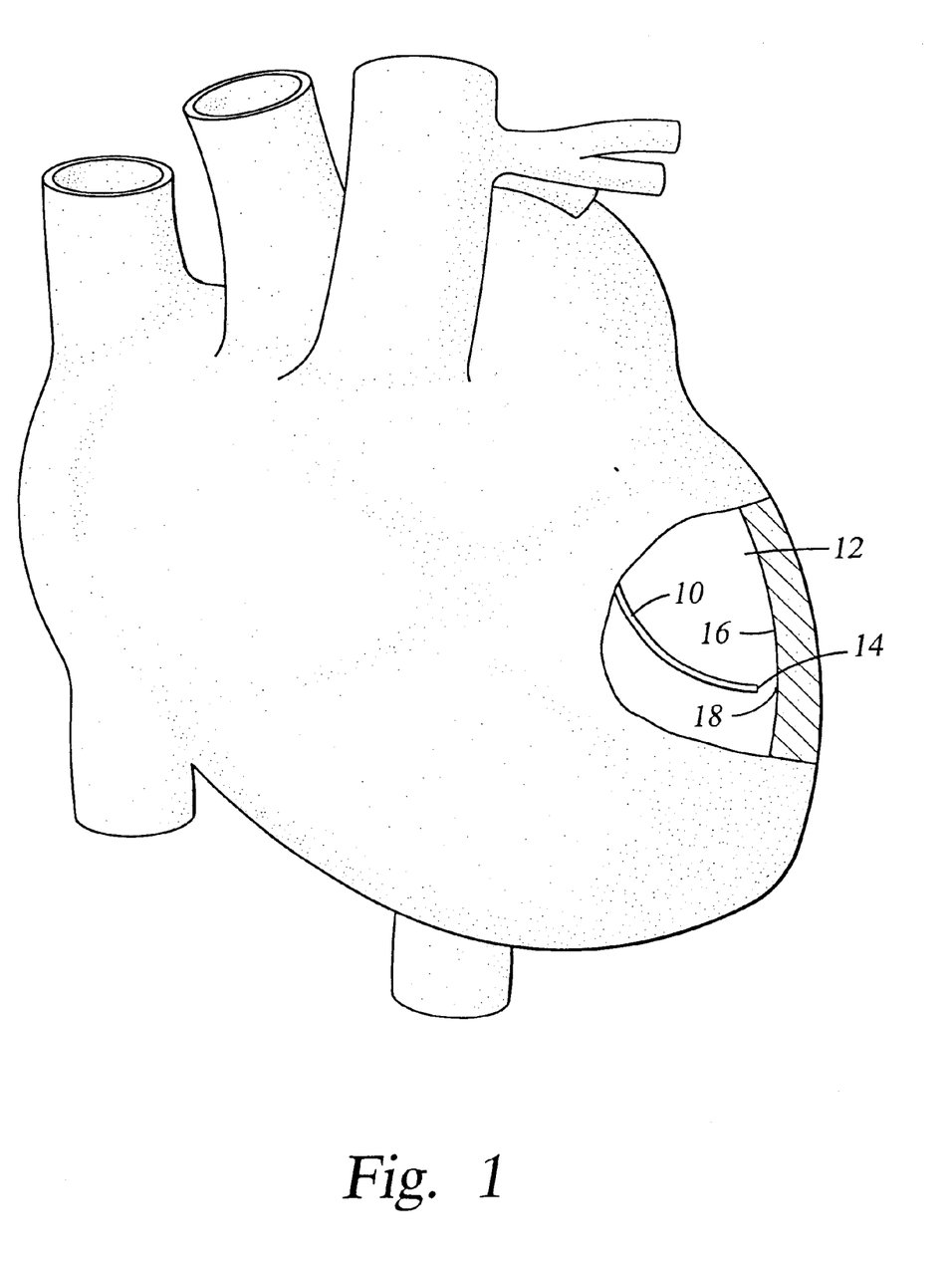
FIG. 1 is a sectional view of a medical device inside a heart.

FIG. 1 is a sectional view of an IMD 10 inside a heart ventricle 12 with the distal end 14 of IMD 10 near the tissue surface 16 at location 18. In order to reach the stage depicted in FIG. 1, medical personnel have had to guide IMD 10 through the patient's blood vessels and into ventricle 12. This global scale guidance of IMD 10 can be accomplished using any of a variety of techniques known in the art and is not the objective of the present invention. The present invention is instead directed towards indicating contact between distal end 14 and a tissue surface 16 at location 18 and, in some embodiments, indicating the perpendicularity of distal end 14 with tissue surface 16. In a TMR procedure, prior to beginning the process of creating channels in the heart wall, the physician may want to confirm that distal end 14 is in contact with and perpendicular to, tissue surface 16 at location 18.

As used in this disclosure, the term distal end will be used to describe both the portion of IMD 10 within the patient (e.g., the opposite of the proximal end), and a point at the "tip" of IMD 10, the furthest from the proximal end. Although, for clarity, the geometry of the distal end 14 of IMD 10 is shown as a flat surface, perpendicular to the longitudinal axis of IMD 10, the present invention is not intended to be limited to any particular configuration.

Figure 2:
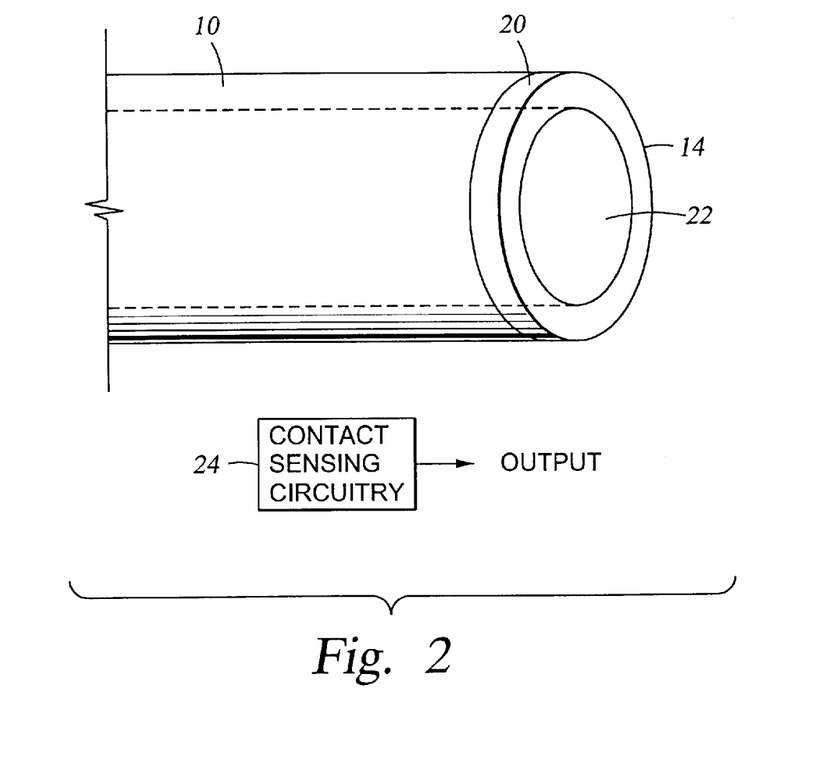
FIG. 2 is an illustration of the distal end of a catheter in accordance with an embodiment of the present invention.

FIG. 2 depicts distal end 14 of IMD 10 in accordance with an embodiment of the present invention. Sensor 20 is shown mounted on IMD 10 at distal end 14. Channel 22, which runs the length of IMD 10, is preferably not obstructed by sensor 20 so that devices such as surgical lasers may pass through sensor 20. Electrical leads, not shown in FIG. 2, connect to sensor 20, run axially through IMD 10, and connect to contact sensing circuitry 24. Contact sensing circuitry 24 then determines the FR characteristics of sensor 20, indicating whether or not distal end 14 is in contact with tissue surface 16 and, in some embodiments, the perpendicularity of IMD 10 to tissue surface 16. Those of ordinary skill in the art will recognize that contact sensing circuitry 24 may be electrically coupled to sensor 22 in ways other than running electrical leads axially through IMD 10, and the present invention is not intended to be limited to any particular method of connecting the components.

In one embodiment of the present invention, sensor 20 is made from a piezoelectric ceramic material with FR characteristics that vary in response to pressure, such as that resulting from contact with tissue surface 16. Using a piezoelectric material for sensor 20 eliminates the need of moving parts, as might be required in an electromechanical switch sensing device.

Although sensor 20 may consist of a piezoelectric material, the present invention does not use sensor 20 as an ultrasound transducer. Instead, sensor 20 is a relatively passive device that utilizes the changes in the internal FR characteristics, as pressure is applied to sensor 20, to detect contact. That is, pressure or force applied to sensor 20 changes the state of stress within the piezoelectric material. This change in the state of stress is, in turn, reflected in the FR characteristics of sensor 20. The piezoelectric embodiment of the present invention utilizes changes in the complex impedance, as measured by magnitude and phase plots of the open loop transfer function, to detect contact. As described more fully below, other embodiments of the present invention utilize FR characteristics other than complex impedance.

Figure 3A:
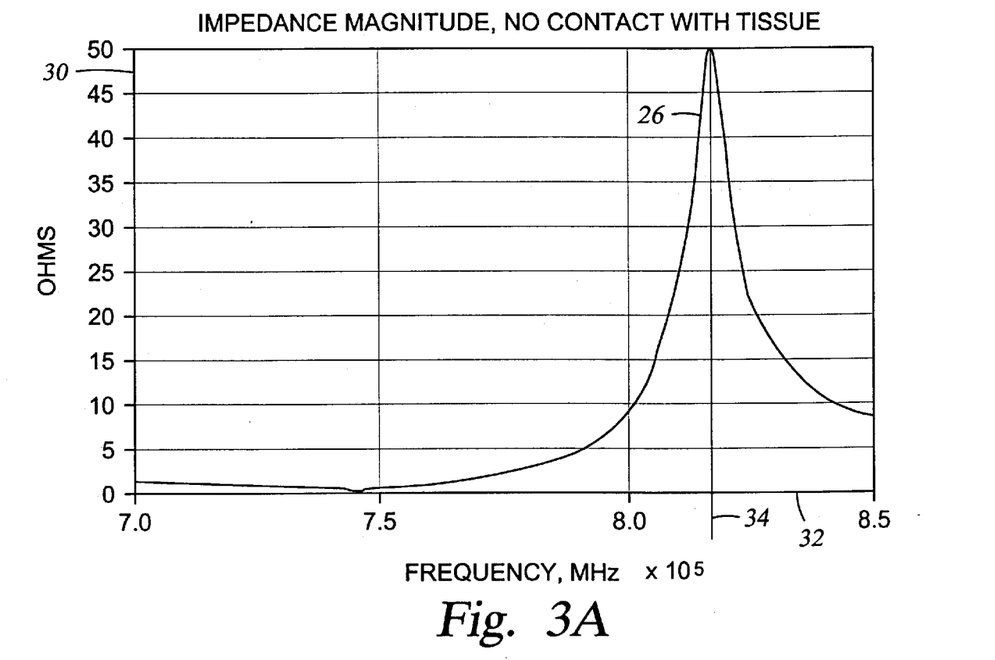
FIG. 3A is a plot of impedance magnitude versus frequency with no contact.
Figure 3B:
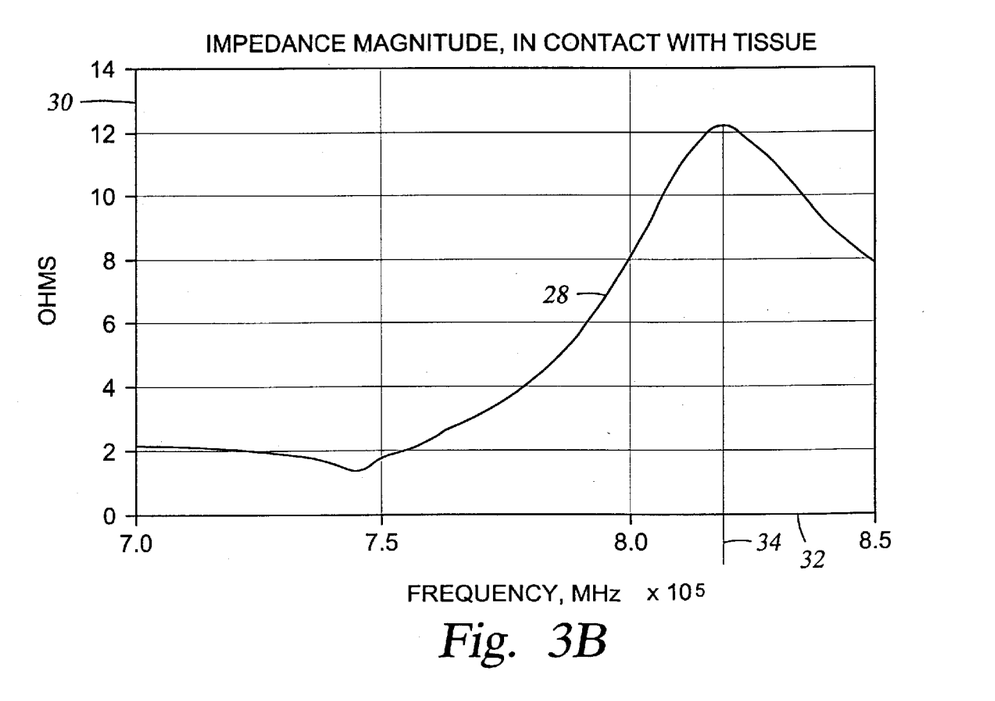
FIG. 3B is a plot of impedance magnitude versus frequency with no contact.

Referring now to FIGS. 3A and 3B, which represent graphs 26 and 28 of impedance magnitude versus frequency for sensor 20 without and with contact, respectively, between distal end 14 and tissue surface 16. Graphs 26 and 28 are "Bode" plots, with linear instead of logarithmic axes, which are known to those of ordinary skill in the control theory art. At the antiresonance frequency 34 (the frequency at which impedance is maximum) of the particular sensor 20, the magnitude of the impedance shifts significantly between the "no contact" and "contact" cases. The magnitude of the impedance shift, seen by comparing between FIGS. 3A and 3B, is approximately a factor of 4.

The particular piezoelectric material used for sensor 20, the size and shape of sensor 20, and the amount of pressure applied to IMD 10 in contact with the tissue may all affect the particular values shown in of Bode plots, as well as the amount of shift observed between no contact and contact states. In this respect, graphs 26 and 28 are merely representative of one particular piezoelectric sensor 20 design, and the present invention is not intended to be limited to any particular sensor 20 design characteristics.

Figure 4A:
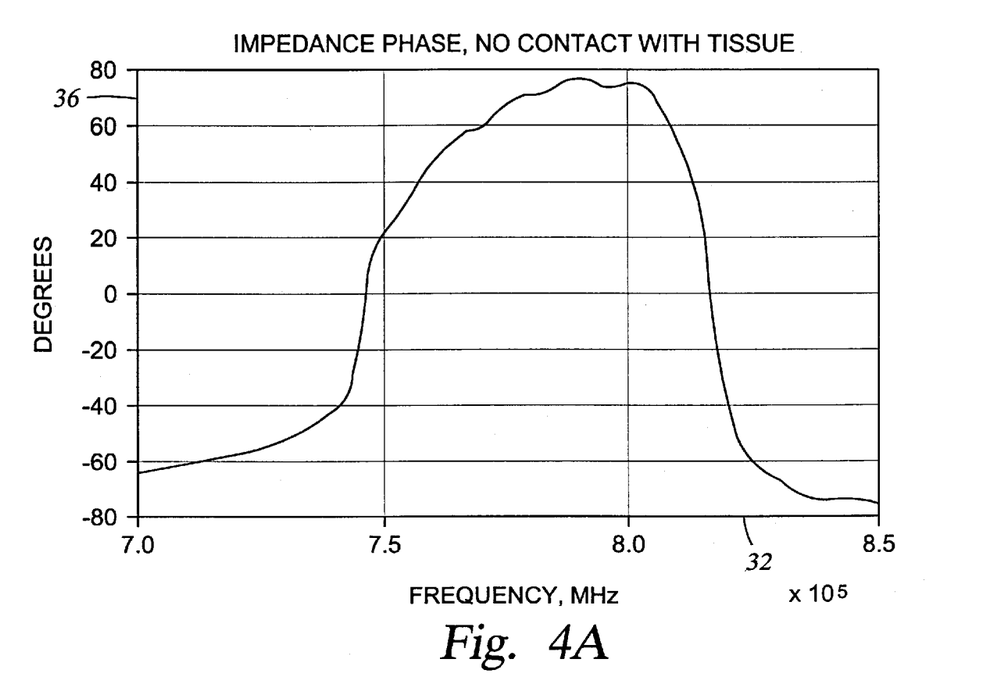
FIG. 4A is a plot of impedance magnitude versus frequency with contact.
Figure 4B:
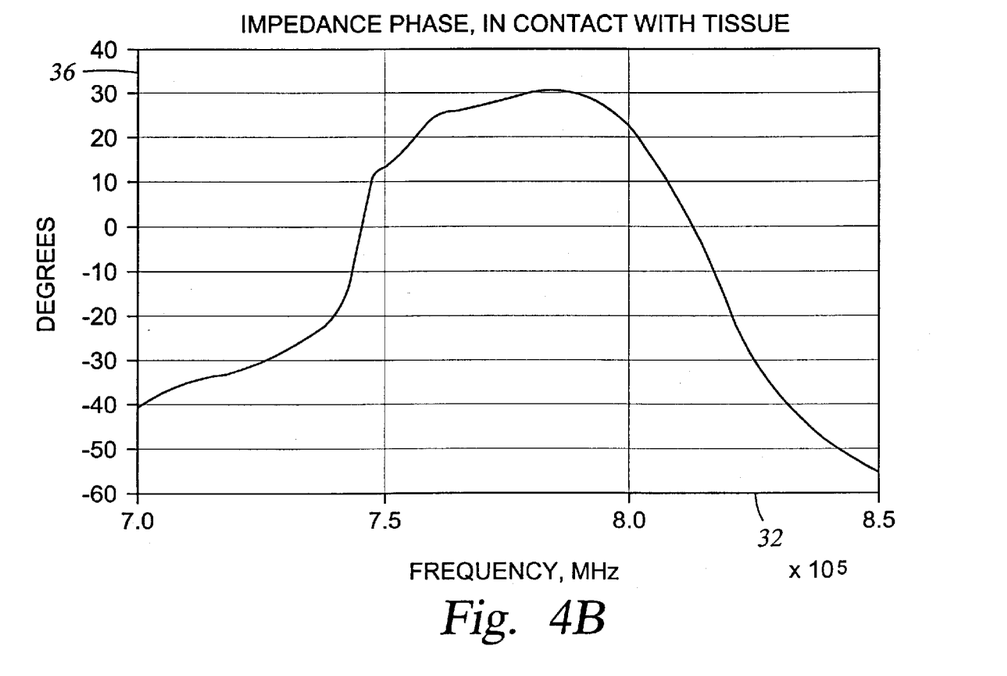
FIG. 4B is a plot of impedance magnitude versus frequency with contact.

FIGS. 4A and 4B are Bode plots of frequency 32 versus impedance phase 36 at antiresonance, for the no contact and contact states respectively. Again, the FR characteristics, now measured as the change in impedance phase 36 at antiresonance, differs significantly between the no contact and contact states. This phase excursion effect may also be used to detect contact between the distal end 14 of IMD 10 and a tissue surface 16 either in conjunction with, or as an alternative to measurement of shifts in impedance magnitude.

One embodiment of the present invention uses an entire no contact Bode plot, similar to those shown in FIGS. 3A and 4A, for comparison with a current FR measurement, made during a medical procedure, to determine whether or not sensor 20 is in contact with tissue surface 16. The no contact Bode plot could be obtained prior to the particular surgical procedure and stored in memory, on a disk, or in any similar storage device known to those of ordinary skill in the art. Preferably, the no contact Bode plot is sampled at an appropriate level of resolution, so that only a digital representation of those samples need to be stored. The current FR measurement would then be compared to the stored data, with contact indicated when there is a sufficient deviation between the stored and current FR characteristics.

Another embodiment of the present invention uses only a few discrete values from the no contact Bode plot for comparison with a current FR measurement. For example, for a given sensor 20, only one, or at most a few, impedance magnitude and/or phase values at, or near, the antiresonance frequency would be stored and tested against current FR to sense contact. The advantages of such an embodiment are that checking few data points requires less time than evaluating an entire graph, and only a small range of frequencies need to be tested. The downside is some loss of accuracy.

In yet another embodiment of the present invention, an entire Bode plot, based on the no contact state, is stored and the impedance at only a few frequencies, sample data points, from the current FR, are compared against those stored points to determine when contact is made with tissue surface 16.

At the heart of the present invention is the difference in the FR properties of sensor 20 between two states, contact and no contact. Those of ordinary skill in the art will recognize that there are a number of algorithms which can be developed to exploit these differences and to indicate whether or not distal end 14 is currently in contact with tissue surface 16. The above embodiments described storing the FR properties of the no contact state, and an expected deviation, for comparison with the current state. That, however, is only one possible technique, and the present invention is not intended to be limited to any particular comparison algorithm. In addition to storing the no contact FR properties with an expected deviation from those properties as a "base case" for later comparisons, at least three other methods may be used.

For example, the no contact FR properties alone may be stored and the amount of deviation from this state, without any expected reference or threshold values, may be used to indicate contact. This deviation would preferably be represented as a single value, such as the difference in the value of the impedance phase at antiresonance from the base case. In another embodiment, both the contact and no contact FR properties are stored with the current FR properties compared to both. The result of such a comparison may be binary state indication (contact or no contact), or a numerical value comparing the current FR properties to the stored range. In yet another embodiment of the present invention, the contact state FR properties are stored as a base case, with or without any expected deviation from those properties for the no contact state With any of the above embodiments of the present invention, either or both of the magnitude and phase of impedance at antiresonance may be used to determine contact between IMD 10 and tissue surface 16. The choice of configuration and material for sensor 20 may dictate increased sensitivity to changes in magnitude or phase of impedance making one of these properties more suitable for use to indicate contact. The other, less contact sensitive, FR property could also be used to increase the accuracy and sensitivity in determining contact. The use of both impedance magnitude and phase may require more processing power, more data storage capability, and perhaps more processing time than examining only a single property. However, the improvement in accuracy and sensitivity may be well worth the additional cost of an apparatus with such additional capability. It is anticipated that the current trend toward faster and less expensive processing power will tend to make such data intensive approaches more popular with time. Conversely, embodiments of the present invention that are directed to speed, or relatively simple logic circuits, would favor less data intensive analysis methods. The present invention is not, however, intended to be limited to any particular technique or related algorithm for detecting contact based changes in the FR characteristics.

As used in the present disclosure, contact sensing circuitry 24 senses the FR characteristics of sensor 20, compares those characteristics with a base case, and creates as output an indication of the current state of sensor 20. That is, contact sensing circuitry 24 can be considered to be a combination of an FR property sensor or measurer, a comparator and an output device. The design details of contact sensing circuitry 24 will depend greatly on the particular embodiment of the present invention. Those of ordinary skill in the art are capable of designing and building a variety of such contact sensing circuitry 24 without undue experimentation. Embodiments of contact sensing circuitry 24 may be implemented in hardware, software, firmware, programmable gate arrays, ASICs, and in various combinations of each. The present invention is not, however, intended to be limited to any particular contact sensing circuitry 24 implementation.

Sensor 20 exhibits changes in FR characteristics based on both the amount of force or pressure applied and to the amount of surface area to which pressure is applied. Embodiments of the present invention using radially symmetric sensor 20 designs, such as shown in FIG. 2, may utilize this geometry to detect the perpendicularity of IMD 10 to tissue surface 16. When IMD 10 is perpendicular to tissue surface 16, at the point of contact, the maximum surface area of sensor 20 is in contact with tissue surface 16, and subject to pressure. The maximum FR changes, in both impedance magnitude and phase, for a given total force on distal end 14, in a manner which corresponds with a perpendicular alignment of IMD 10 relative to tissue surface 16. For a given type of procedure, such as a TMR, the maximum and expected forces applied at distal end 14 of IMD 10, may be estimated in advance. Changes in the FR characteristics, of less than the maximum expected when the maximum force is applied to distal end 14, can be used to indicate a non-perpendicular orientation to tissue surface 16.

Figure 5:
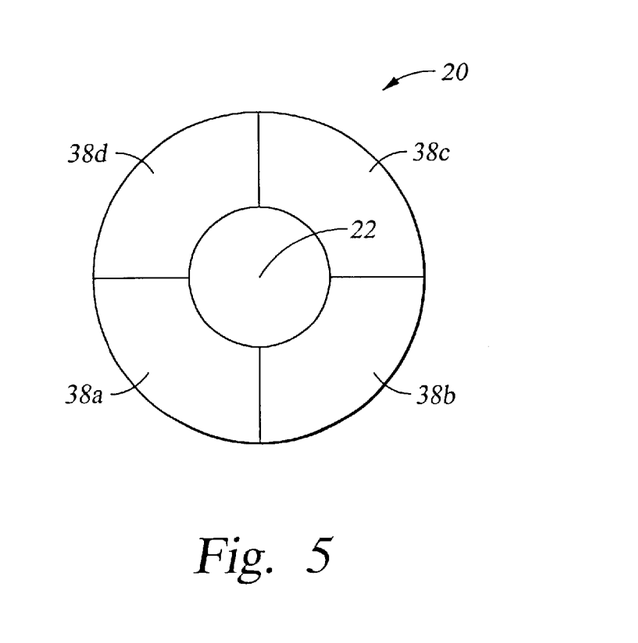
FIG. 5 is an illustration of a multiple segment sensor in accordance with an embodiment of the present invention.

FIG. 5 illustrates one embodiment of the present invention using a sensor 20 divided in four segments 38a through 38d. The embodiment shown in FIG. 5 allows for individual contact, and pressure, indications from each segment. Although the data to evaluate increases compared to a single ring-like embodiment, those of ordinary skill in the art will recognize that such segments 38 allow for more precise perpendicularity indications. Although FIG. 5 uses four segments, the present invention is not intended to be limited to any particular number of segments. Preferably, some of the segments 38a through 38d are arranged so that they coincide with the steering axes of IMD 10.

In addition to the above descriptions of embodiments of the present invention, using piezoelectric ceramic materials, other embodiments for sensing changes in the FR based upon a change in inductance.

Figure 6:
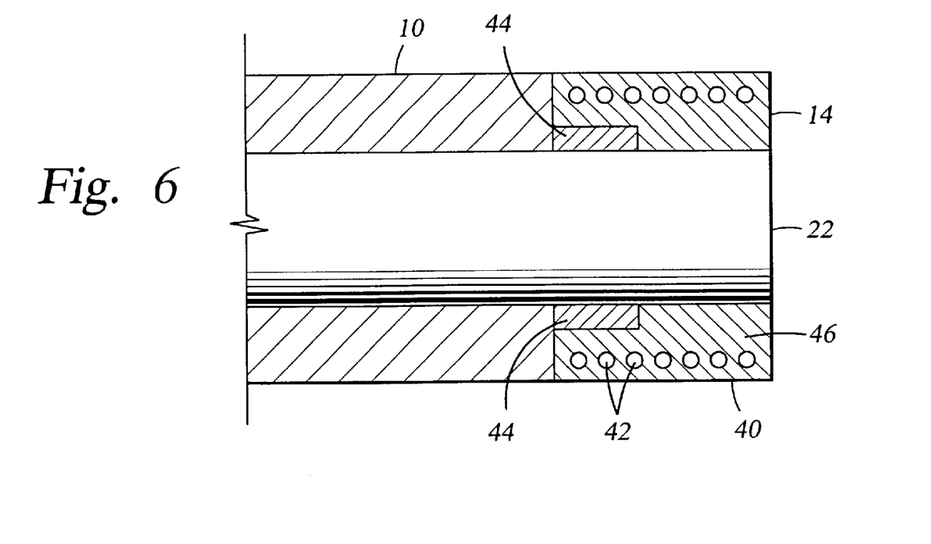
FIG. 6 is an illustration of the distal end of a catheter in accordance with an embodiment of the present invention.

FIG. 6, illustrates a distal end 14 of an IMD 10 which has an induction based sensor 40. Sensor 40, like the embodiment shown in FIG. 2, surrounds a channel 22 so that devices such as surgical lasers may pass through IMD 10 and sensor 40. Sensor 40 includes one or more electrically conductive coil windings 42, oriented essentially perpendicular to the longitudinal axis of IMD 10, and essentially perpendicular to an iron core 44. Windings 42 are embedded within a compliant matrix material 46, so that the material will compress significantly with pressure. Preferably, material 46 will have a Shore-A value of 40, or lower, as measured on a durometer, and will be biologically inert when introduced into a patient's body.

Figure 7:
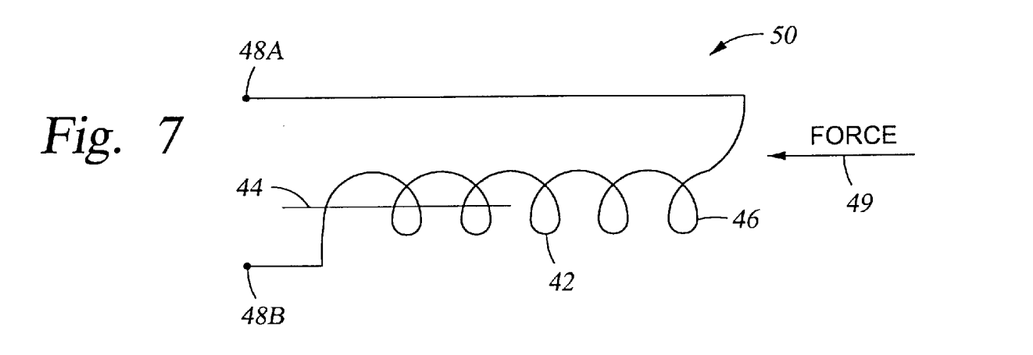
FIG. 7 is a schematic representation of an embodiment of the present invention.

As distal end 14 comes into contact with a tissue surface (not shown), material 46 compresses causing more windings 42, to encircle iron core 44. It is known to those of ordinary skill in the art that inserting an iron core into inductor coil causes the inductance of the coil to increase. Thus, the compression of material 46, from contact between distal end 14 and tissue surface 16, causes a change in inductance. A schematic representation of the electro-magnetically active components of sensor 40 are shown in FIG. 7. Windings 42 form an inductor 46, around iron core 44, with electrical connections 48. Force 49 causes the properties of inductor 46 to change as the position of iron core 44 changes relative to windings 42. The change in inductance, which is correlated to the amount compression, can be detected as a change in the FR of a circuit containing coils 42.

Those of ordinary skill in the art, with benefit of the current disclosure, will recognize that inductor 46 and iron core 44 may take on many configurations consistent with the well developed art of inductors and inductor cores, and the present invention is not intended to be limited to any particular configuration. For example, the term "iron core" as used in the present disclosure is functional, and is not intended to limit the material used for iron core 44 to iron, but may include other chemicals or compounds suitable for inductor cores.

In another embodiment of the present invention, windings 42 of inductor 46 are essentially stationary, while iron core 44 moves in response to contact between distal end 14 and tissue surface 16. The change in the number of windings 42 around iron core 44 is what causes the inductance to change, whether the movement is by windings 42 or iron core 44.

Figure 8:
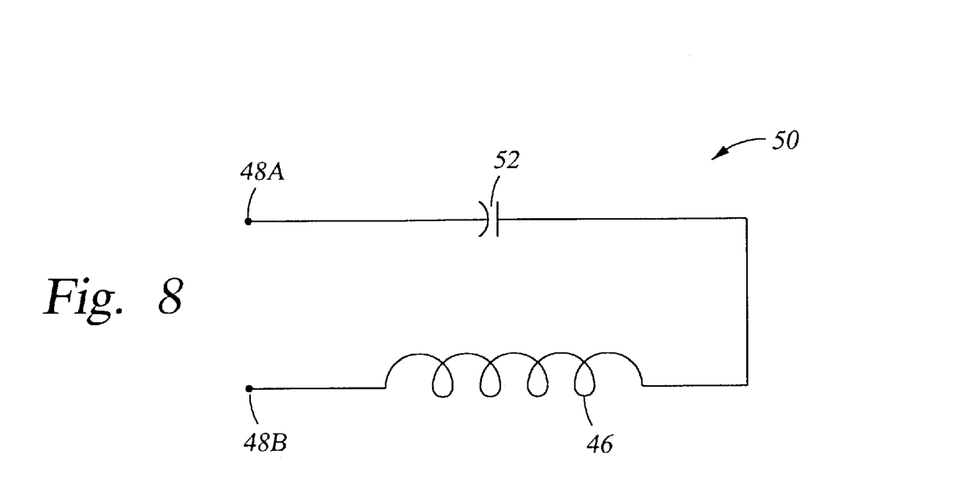
FIG. 8 is a LC circuit formed by an embodiment of the present invention.

The present invention uses an LC circuit 50, as shown in FIG. 8 to sense changes in the FR characteristics, and detect contact with tissue surface 16. Capacitor 52 is connected in series to inductor 46 and electrical connections 48a and 48b. A variable frequency alternating current is applied to electrical connections 48a and 48b in order to determine the resonant frequency of LC circuit 50.

Using the formula:

$$f = \frac{1}{2\pi\sqrt{LC}}$$

where; f equals the resonant frequency, L the inductance and C the capacitance. Testing for the resonant frequency in LC circuit 50, with the value of capacitance C known, yields the value of inductance L. The value of inductance L varies with the relative movement of windings 42 and iron core 44, thus indicating contact.

The frequencies used with LC circuit 50 will preferably span from the range of resonance frequencies of sensor 40 in the contact and no contact states. For a given sensor 40 design, or configuration, capacitor 52 is chosen so that the resonance frequency may be easily determined. Those of ordinary skill in the art are able to find the resonance frequency of LC circuit 50 using variable frequency signals.

In one embodiment of the present invention, the change in inductance L is used to indicate perpendicularity. For a constant force 49, the inductance L will be the largest when IMD 10 is perpendicular to tissue surface 16.

Figure 9:
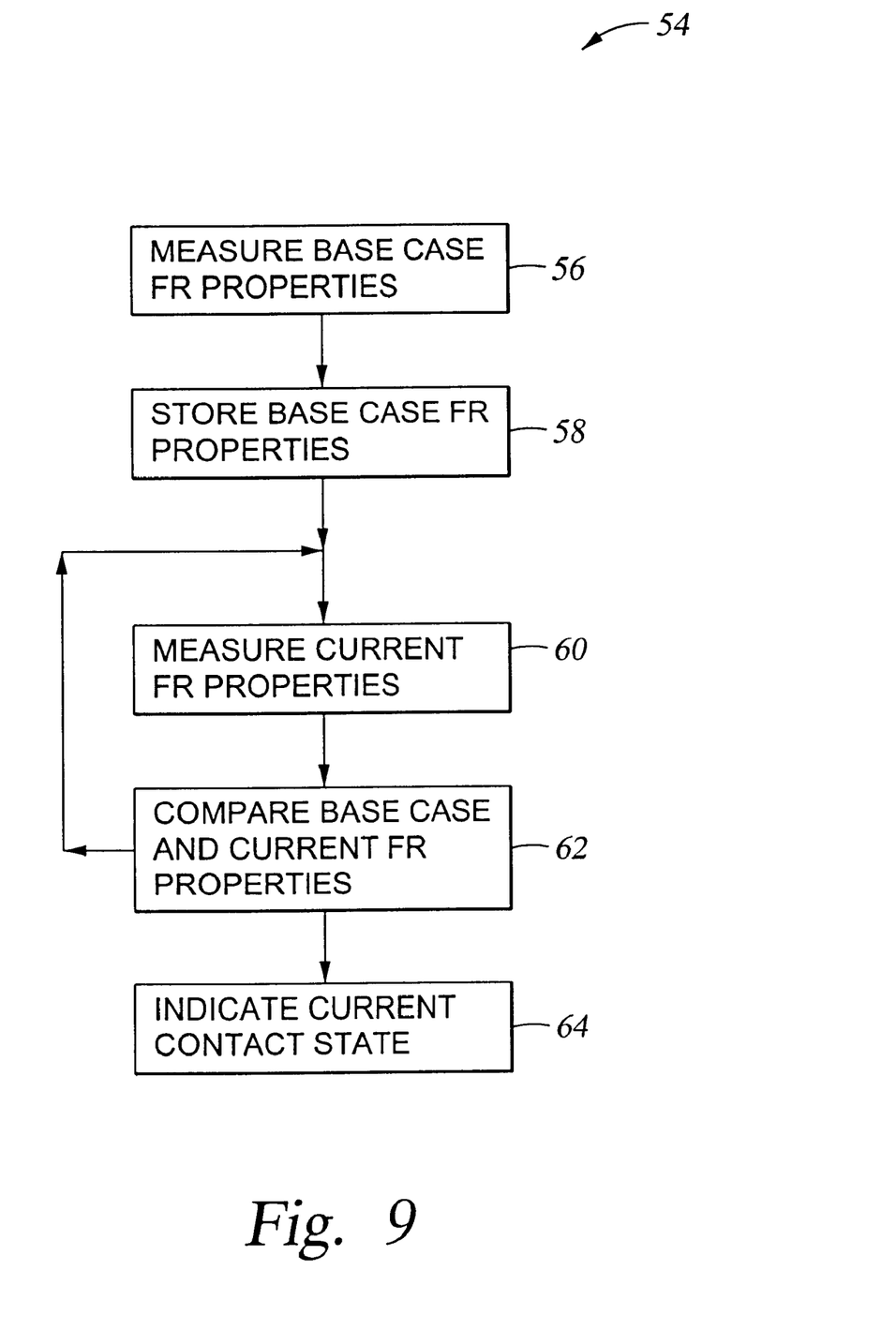
FIG. 9 is a flow chart of determining contact between the distal end of a catheter and the tissue surface in accordance with an embodiment of the present invention.

FIG. 9 is a flow chart 54 of a method used by an embodiment of the present invention to determine contact between the distal end of an IMD and a tissue surface. The process shown in FIG. 9 applies to both piezoelectric ceramic and inductive coil embodiments of the present invention. Initially, baseline measurements of the FR properties are made 56 and stored 58. These steps could be performed well in advance of the surgical procedures and should remain relatively constant for a particular sensor configuration in a particular medical environment. Next, at some point during a surgical procedure, such as when distal end 14 is within the heart during a TMR procedure, monitoring of the current FR properties begins 60. Preferably, this monitoring process is repeated continuously throughout the surgical procedure to give real time, or near real time contact information. A comparison 62 is made between the current FR properties and the stored baseline measurements and, a contact indication 64 is given. Repeating process 60 continuously allows the contact indication to show current state of contact. Those of ordinary skill in the art, given the present disclosure, will be able to adapt the processes in FIG. 9 to also indicate the perpendicularity of IMD 10 to tissue surface 16.

While embodiments and applications of this invention have been shown and described, it would be apparent to those skilled in the art, after a review of this disclosure, that many more modifications than mentioned above are possible without departing from the inventive concepts herein. The invention, therefore, is not to be restricted except in the spirit of the appended claims.

What is claimed is:

1. A method of indicating when the distal end of an interventional medical device (IMD) is in contact with a tissue surface, comprising:
    mounting a sensor, with frequency response (FR) properties that vary with pressure, on the distal end of the IMD;
    measuring an initial set of FR properties, said initial set of properties corresponding to a base case;
    storing said initial set of FR properties;
    measuring a current set of FR properties;
    comparing said initial set of properties and said current set of FR properties; and
    reporting a contact state.

2. A method in accordance with claim 1, wherein:
    measuring said initial set and said current set of FR properties is performed using variable frequency signals to determine impedance magnitude at antiresonance.

3. A method in accordance with claim 1, wherein:
    measuring said initial set and said current set of FR properties is performed using variable frequency signals to determine impedance phase at antiresonance.

4. A method in accordance with claim 1, wherein.
    measuring said initial set and said current set of FR properties is performed using variable frequency both impedance magnitude and phase at antiresonance.

5. A method in accordance with claim 1, wherein:
    measuring said initial set of FR properties comprises creating an initial Bode plot.

6. A method in accordance with claim 5, wherein:
    said Bode plot is impedance magnitude versus frequency.

7. A method in accordance with claim 5, wherein:
    said Bode plot is impedance phase versus frequency.

8. A method in accordance with claim 1, wherein:
    measuring said initial set of FR properties comprises measuring a single impedance magnitude value.

9. A method in accordance with claim 1, wherein:
    measuring said initial set of FR properties comprises measuring a single impedance phase value.

10. A method in accordance with claim 1, wherein:
    measuring said initial set of FR properties comprises measuring a single impedance magnitude and a single impedance phase value.

11. A method in accordance with claim 1, wherein:
measuring said initial set of FR properties comprises measuring a plurality of discrete impedance magnitude values.

12. A method in accordance with claim 1, wherein:
measuring said initial set of FR properties comprises measuring a plurality of discrete impedance phase values.

13. A method in accordance with claim 1, wherein:
measuring said initial set of FR properties comprises measuring a plurality of impedance magnitude values and impedance phase values.

14. A method in accordance with claim 13, wherein:
said plurality of impedance magnitude values and said impedance phase values are taken at a common set of frequencies.

15. A method in accordance with claim 5, wherein:
storing said initial set of FR properties involves sampling values from said initial Bode plot.

16. A method in accordance with claim 15, wherein:
measuring said current set of FR properties comprises creating a current Bode plot.

17. A method in accordance with claim 15, wherein:
measuring said current set of FR properties comprises measuring an impedance magnitude value.

18. A method in accordance with claim 15, wherein:
measuring said current set of FR properties comprises measuring an impedance phase value.

19. A method in accordance with claim 1, further comprising:
measuring a perpendicularity of the IMD with the tissue surface.

20. A method in accordance with claim 1, wherein:
measuring said initial set and said current set of FR properties is performed using variable frequency signals to determine an LC circuit resonant frequency.

21. A device to sense contact between the distal end of an interventional medical device (IMD) and a tissue surface, comprising:
a sensor, adapted for mounting on the distal end of the IMD, said sensor with frequency response (FR) properties that change between a no contact state and a contact state in response to pressure;
an FR property measurer electrically coupled to said sensor for measuring a current set of FR properties; and
a comparator coupled to said FR property measurer for evaluating a current state from said current set of FR properties and indicating said current state.

22. A device in accordance with claim 21, wherein:
said FR property measurer produces an impedance magnitude versus frequency plot.

23. A device in accordance with claim 21, wherein:
said FR property measurer produces an impedance phase versus frequency plot.

24. A device in accordance with claim 21, wherein:
said FR property measurer produces plots of both an impedance magnitude versus frequency and an impedance phase versus frequency.

25. A device in accordance with claim 21, wherein:
said sensor contains a piezoelectric material.

26. A device in accordance with claim 21, wherein:
said sensor is responsive to a perpendicularity between the IMD and the tissue surface.

27. A device in accordance with claim 21, wherein:
said sensor is a variable inductance coil.

28. A device for use in a transmyocardial revascularization (TMR) procedure to indicate when the distal end of a catheter comes into contact with a tissue surface, comprising:
a contact sensor with at least one pressure sensitive frequency (FR) response property, said contact sensor adapted to mount on the distal end of the catheter; and
an FR property tester coupled to said contact sensor for monitoring FR properties of said contact sensor and indicating a contact state.

29. A device for use in a transmyocardial revascularization (TMR) procedure to indicate when the distal end of a catheter comes into contact with a tissue surface, comprising:
a contact sensor with at least one pressure sensitive frequency response (FR) property selected from the group consisting of impedance magnitude, impedance phase, and combinations thereof, said contact sensor adapted to mount on the distal end of the catheter; and
an FR property tester coupled to said contact sensor for monitoring said at least one pressure sensitive FR property of said contact sensor and indicating a contact state.

30. A device to sense when contact is made between the distal end of an interventional medical device (IMD) and a tissue surface, comprising:
a sensor, adapted for mounting on the distal end of the IMD, said sensor having at least one frequency response (FR) property selected from the group consisting of impedance magnitude, impedance phase, and combinations thereof, that changes between a no contact state and a contact state in response to pressure;
an FR property measurer electrically coupled to said sensor for measuring a current state from said current set of FR properties and indicating said current state.

* * * * *